US007833251B1

(12) United States Patent
Ahlgren et al.

(10) Patent No.: US 7,833,251 B1
(45) Date of Patent: Nov. 16, 2010

(54) SYSTEM AND METHOD FOR PERFORMING SPINAL FIXATION

(75) Inventors: Dan Ahlgren, San Diego, CA (US); Bret Ferree, Cincinnati, OH (US); Keith Valentine, San Diego, CA (US); Patrick Miles, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1014 days.

(21) Appl. No.: 11/031,506

(22) Filed: Jan. 6, 2005

Related U.S. Application Data

(60) Provisional application No. 60/534,650, filed on Jan. 6, 2004.

(51) Int. Cl.
*A61B 17/88* (2006.01)
(52) U.S. Cl. .................. 606/279; 606/264; 606/265; 606/278
(58) Field of Classification Search .............. 606/60, 606/61, 250–279, 86 A
See application file for complete search history.

(56) References Cited

U.S. PATENT DOCUMENTS

| | | | |
|---|---|---|---|
| 4,361,141 A | 11/1982 | Tanner | |
| 4,771,767 A | 9/1988 | Steffee | |
| 4,805,602 A | 2/1989 | Puno et al. | |
| 4,946,458 A | 8/1990 | Harms et al. | |
| 4,998,936 A | 3/1991 | Mehdian | |
| 5,034,011 A | 7/1991 | Howland | |
| 5,042,982 A | 8/1991 | Harms et al. | |
| 5,084,049 A | 1/1992 | Asher et al. | |
| 5,092,866 A | 3/1992 | Breard et al. | |
| 5,092,867 A | 3/1992 | Harms et al. | |
| 5,129,388 A | 7/1992 | Vignaud et al. | |
| 5,176,680 A | 1/1993 | Vignaud et al. | |
| 5,196,013 A | 3/1993 | Harms et al. | |
| 5,207,678 A | 5/1993 | Harms et al. | |
| 5,234,431 A * | 8/1993 | Keller .................... | 606/70 |
| 5,261,907 A | 11/1993 | Vignaud et al. | |
| 5,275,600 A | 1/1994 | Allard et al. | |
| 5,312,405 A | 5/1994 | Korotko et al. | |
| 5,330,473 A | 7/1994 | Howland | |
| 5,375,823 A | 12/1994 | Navas | |
| 5,387,213 A | 2/1995 | Breard et al. | |
| 5,466,237 A | 11/1995 | Byrd, III et al. | |
| 5,474,555 A | 12/1995 | Puno et al. | |
| 5,478,340 A | 12/1995 | Kluger | |

(Continued)

FOREIGN PATENT DOCUMENTS

DE          3722590 C1    12/1988

(Continued)

OTHER PUBLICATIONS

Beadling, "Harrington put the steel in spinal fixation",*Orthopedics Today*, (Jun. 2000).

(Continued)

*Primary Examiner*—Eduardo C Robert
*Assistant Examiner*—Tara R Carter
(74) *Attorney, Agent, or Firm*—Jonathan Spangler; Rory Schermerhorn

(57) ABSTRACT

The present invention relates to medical devices and methods generally aimed at spinal surgery. In particular, the disclosed system and associated methods relate to performing spinal fixation.

20 Claims, 13 Drawing Sheets

U.S. PATENT DOCUMENTS

| | | | |
|---|---|---|---|
| 5,480,401 A | | 1/1996 | Navas |
| 5,505,731 A | * | 4/1996 | Tornier .................. 606/261 |
| 5,536,268 A | | 7/1996 | Griss |
| 5,540,688 A | | 7/1996 | Navas |
| 5,545,163 A | * | 8/1996 | Miller et al. ............. 606/287 |
| 5,545,166 A | | 8/1996 | Howland |
| 5,607,425 A | | 3/1997 | Rogozinski |
| 5,624,442 A | | 4/1997 | Mellinger et al. |
| 5,630,816 A | | 5/1997 | Kambin |
| 5,643,264 A | | 7/1997 | Sherman et al. |
| 5,645,544 A | | 7/1997 | Tai et al. |
| 5,665,122 A | | 9/1997 | Kambin |
| 5,667,508 A | | 9/1997 | Errico et al. |
| 5,669,911 A | | 9/1997 | Errico et al. |
| 5,672,176 A | | 9/1997 | Biedermann et al. |
| 5,676,665 A | | 10/1997 | Bryan |
| 5,690,630 A | | 11/1997 | Errico et al. |
| 5,704,936 A | | 1/1998 | Mazel |
| 5,716,355 A | | 2/1998 | Jackson et al. |
| 5,725,527 A | | 3/1998 | Biedermann et al. |
| 5,776,135 A | | 7/1998 | Errico et al. |
| 5,800,435 A | | 9/1998 | Errico et al. |
| 5,863,293 A | | 1/1999 | Richelsoph |
| 5,873,878 A | | 2/1999 | Harms et al. |
| 5,928,232 A | | 7/1999 | Howland et al. |
| 5,928,237 A | | 7/1999 | Farris et al. |
| 5,938,663 A | | 8/1999 | Petreto |
| 5,944,719 A | | 8/1999 | Leban |
| 5,944,720 A | | 8/1999 | Lipton |
| 5,947,966 A | | 9/1999 | Drewry et al. |
| 5,951,555 A | | 9/1999 | Rehak et al. |
| 5,954,722 A | | 9/1999 | Bono |
| 5,954,725 A | | 9/1999 | Sherman et al. |
| 5,961,516 A | | 10/1999 | Graf |
| 5,980,523 A | | 11/1999 | Jackson |
| 6,030,389 A | | 2/2000 | Wagner et al. |
| 6,063,089 A | | 5/2000 | Errico et al. |
| 6,074,391 A | * | 6/2000 | Metz-Stavenhagen et al. . 606/61 |
| 6,113,600 A | | 9/2000 | Drummond et al. |
| 6,136,003 A | | 10/2000 | Hoeck et al. |
| 6,139,548 A | | 10/2000 | Errico |
| 6,190,388 B1 | | 2/2001 | Michelson et al. |
| 6,217,578 B1 | | 4/2001 | Crozet et al. |
| 6,224,598 B1 | * | 5/2001 | Jackson ..................... 606/61 |
| 6,234,705 B1 | | 5/2001 | Troxell |
| 6,241,730 B1 | | 6/2001 | Alby |
| 6,264,658 B1 | | 7/2001 | Lee et al. |
| 6,267,765 B1 | * | 7/2001 | Taylor et al. .............. 606/61 |
| 6,273,914 B1 | * | 8/2001 | Papas .................... 623/17.11 |
| 6,283,967 B1 | | 9/2001 | Troxell et al. |
| 6,296,644 B1 | | 10/2001 | Saurat et al. |
| 6,306,137 B2 | | 10/2001 | Troxell |
| 6,325,802 B1 | | 12/2001 | Frigg |
| 6,379,354 B1 | | 4/2002 | Rogozinski |
| 6,899,714 B2 | * | 5/2005 | Vaughan ................ 606/86 A |
| 2001/0034521 A1 | | 10/2001 | Bailey et al. |
| 2004/0260287 A1 | | 12/2004 | Ferree |
| 2005/0010217 A1 | * | 1/2005 | Dalton ..................... 606/61 |

FOREIGN PATENT DOCUMENTS

| | | |
|---|---|---|
| DE | 3841008 | 6/1990 |
| DE | 9004960 U | 8/1991 |
| DE | 9219204 | 12/1999 |
| EP | 0128058 A1 | 12/1984 |
| EP | 0283373 A1 | 9/1988 |
| EP | 0348272 A1 | 12/1989 |
| EP | 1072228 A1 | 1/2001 |
| FR | 2559378 A1 | 8/1985 |
| FR | 2624720 A1 | 6/1989 |
| WO | WO-9722306 A1 | 6/1997 |

OTHER PUBLICATIONS

Dipreta, "The Illiac Nail/Screw: A Modified . . . ", *Am. Acad. of Ortho. Surg., 67th mtg., PE184*, (Mar. 19, 2000).

Ebrahim, "Posterior Lateral Mass Screw Fixation . . . ", *U.P.O.J.*, vol. 12, (Spring 1999),66-72.

Erickson, "Biomechanical Assessment of . . . ", *Am. Acad. of Ortho. Surg., 2002 mtg., P217*, (Mar. 13, 2002).

Pham, "Upper Cervical Spine Surgery in . . . ", *Joint Bone Spine 2000*, 67, (2000),434-440.

Sanders, "Treating, managing spinal deformity in young patients", *Orthopedics today*, (Jul. 2001).

Spiegel, "Anterior instrumentation in the Treatment . . . ", *U.P.O.J.*, vol. 11, (Spring 1998), 19-26.

Wood, "Torsional Rigidity of Scoliosis Constructs", *Am. Acad. of Ortho. Surg., PE123*, (Feb. 4, 1999).

* cited by examiner

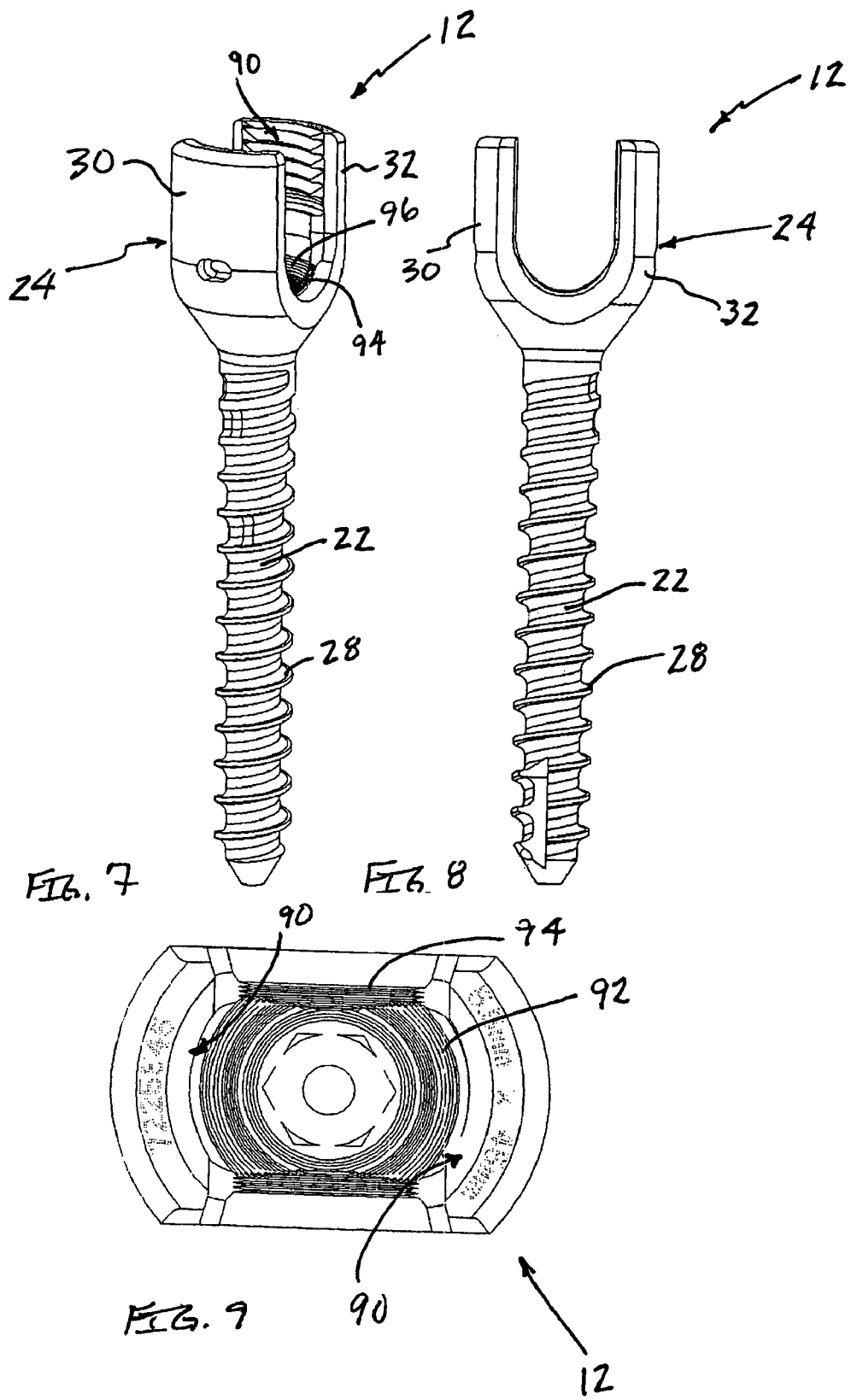

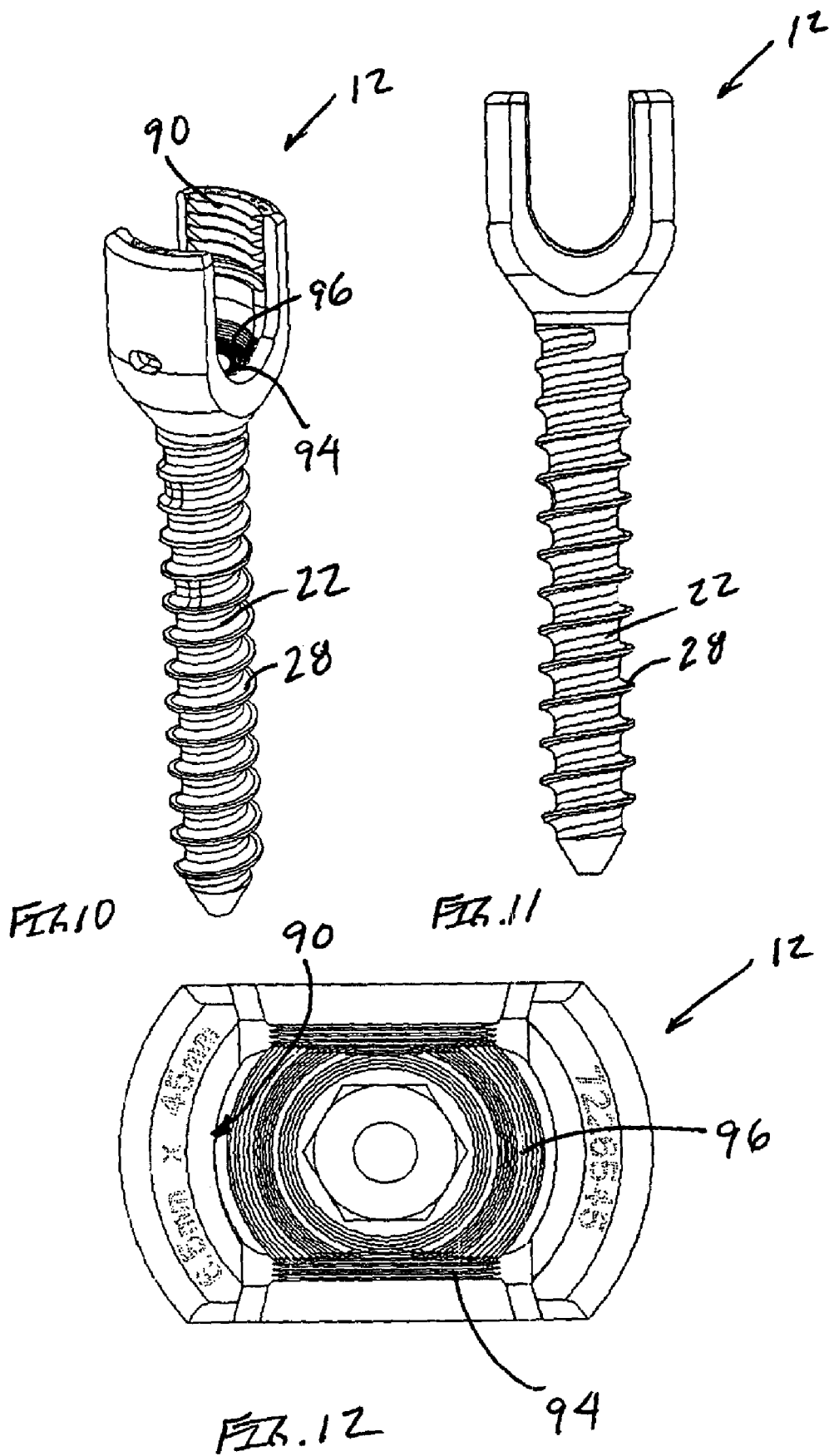

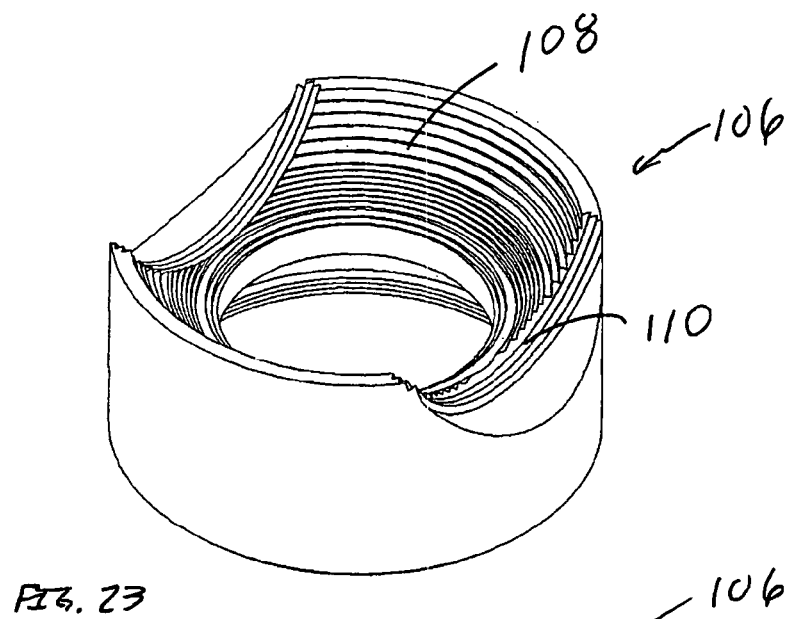
FIG. 23
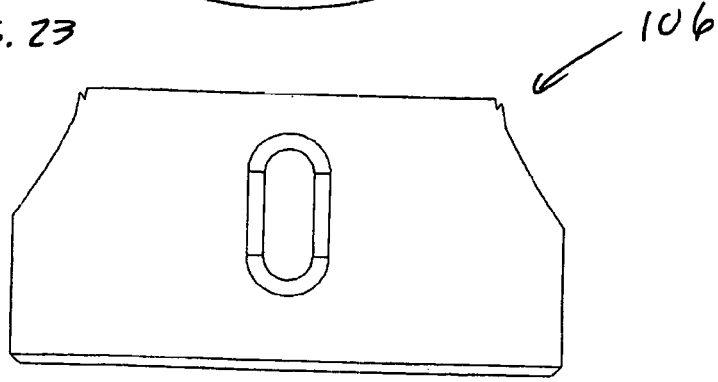
FIG. 24
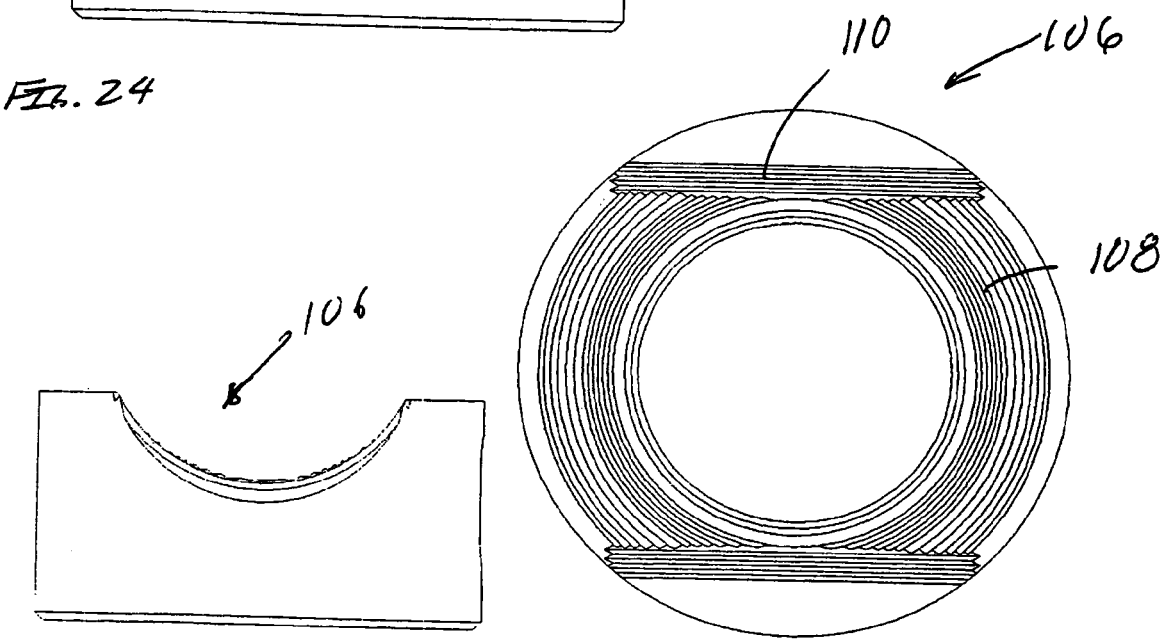
FIG. 25
FIG. 26

SYSTEM AND METHOD FOR PERFORMING SPINAL FIXATION

CROSS REFERENCES TO RELATED APPLICATIONS

The present application is a nonprovisional patent application claiming benefit under 35 U.S.C. §119(e) from U.S. Provisional Application Ser. No. 60/534,650, filed on Jan. 6, 2004, the entire contents of which are hereby expressly incorporated by reference into this disclosure as if set forth fully herein.

BACKGROUND OF THE INVENTION

I. Field of the Invention

The present invention relates to medical devices and methods generally aimed at spinal surgery. In particular, the disclosed system and associated methods relate to performing spinal fixation.

II. Discussion of the Prior Art

Fixation systems are often surgically implanted into a patient to aid in the stabilization of a damaged spine or to aid in the correction of other spinal geometric deformities. Spinal fixation systems are often constructed as a framework stabilizing a particular section of the spine. Existing systems often use a combination of rods, plates, pedicle screws and bone hooks for fixing the framework to the affected vertebrae. The configuration required for each patient varies due to the patient's specific anatomical characteristics and ailments. As a result, there is a need for a modular spinal fixation system that allows for a large degree of custom configurations.

The present invention is directed at addressing this need and eliminating, or at least reducing, the effects of the shortcomings of the prior art systems as described above.

SUMMARY OF THE INVENTION

The present invention discloses a system and methods for performing spinal fixation. The system includes at least one pair of elongate members, a plurality of pedicle screws and at least one transverse connector.

The elongate members are installed along the length of the spine of the patient. The elongate members are coupled to vertebrae by a set of pedicle screws. In addition, to increase the rigidity of the fixation system, at least one transverse connector may be used to interconnect the elongate members.

The elongate members may include rods with sufficient length to span the affected area. The rods are constructed with an outer surface that is compatible with the head of a pedicle screw, bone hook or transverse connector. The elongate member may be of a length sufficient to span the entire length of the affected spinal section. Alternatively, the elongate members may be constructed from a plurality of the members coupled together.

Pedicle screws are included to couple the elongate rod members to the bony structures in the spine. Pedicle screws may have heads that are rigid with respect to the screw shank or heads that may be angularly adjusted with respect to the screw shank. As used herein, a poly-axial pedicle screw shall be understood to encompass the latter configuration.

The transverse connectors are designed to extend between and couple a pair of elongate members. The transverse connectors are adjustable in length along the longitudinal axis and both ends are able to rotate along the longitudinal axis. Furthermore, the angle of each end with respect to the longitudinal axis is adjustable.

BRIEF DESCRIPTION OF THE DRAWINGS

Other objects and advantages of the invention will become apparent upon reading the following detailed description and upon reference to the drawings in which:

FIGS. 7-9 are perspective, side and top views, respectively, of a fixed angle pedicle screw assembly of the present invention, having a shaft diameter of 5.5 mm and a length of 45 mm;

FIGS. 10-12 are perspective, side and top views, respectively, of a fixed angle pedicle screw assembly of the present invention, having a shaft diameter of 6.5 mm and a length of 45 mm;

FIGS. 23-26 are perspective, first side, second side, and top views, respectively, of a load ring forming part of the poly-axial pedicle screw system of the present invention.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and method for performing spinal fixation disclosed herein boast a variety of inventive features and components that warrant patent protection, both individually and in combination.

Figure 1:
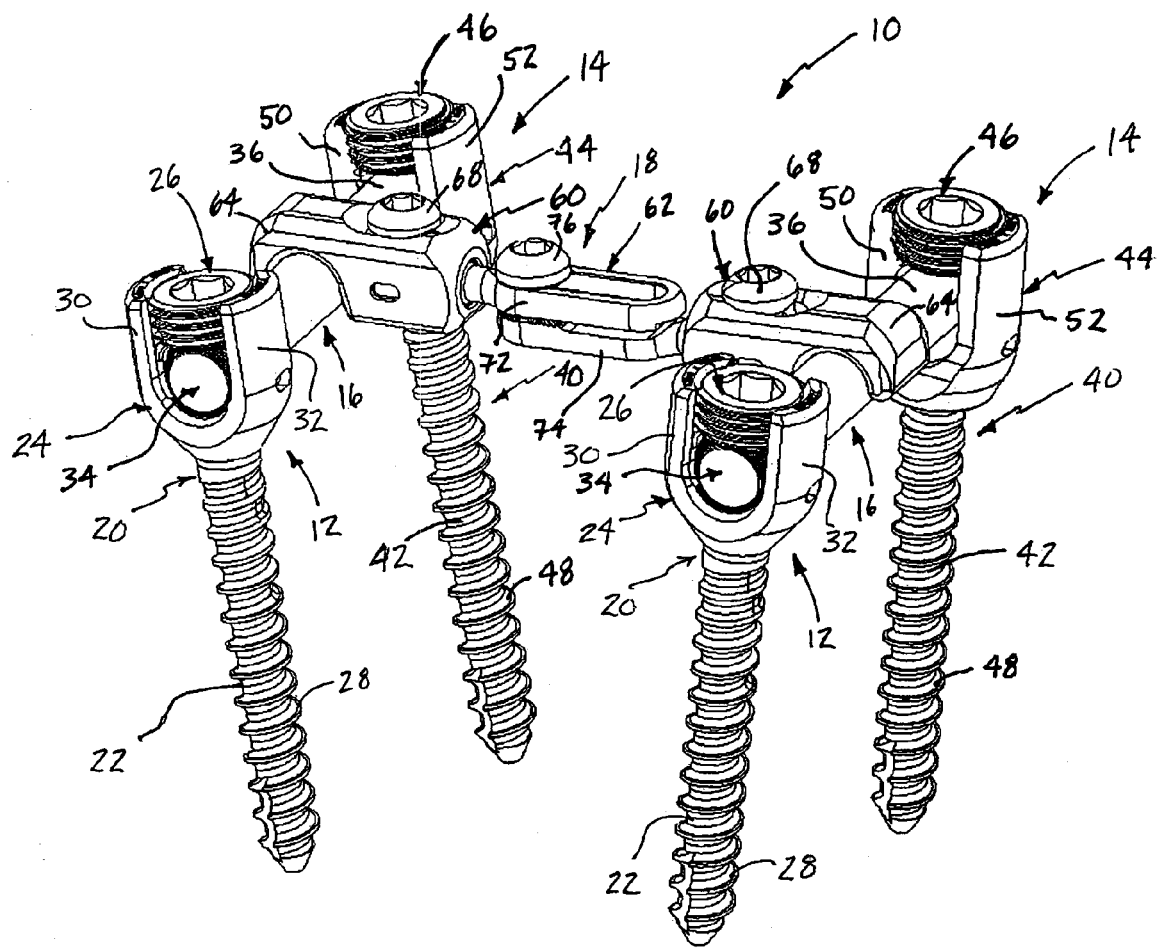
FIG. 1 is a perspective view of a spinal fixation system of the present invention incorporating (by way of example only) a single axis pedicle screw, a poly-axial pedicle screw, a spherical-ended rod member, and a transverse connector, each forming a unique and patentable aspect of the present invention.

FIG. 1 is a perspective view of a spinal fixation system 10 of the present invention. The spinal fixation system 10 is suitable for effecting fixation between adjacent vertebral levels within the spine. The spinal fixation system 10 of the present invention as shown in this embodiment includes a pair single axis or "fixed" pedicle screw assemblies 12, a pair of poly-axial pedicle screw assemblies 14, a pair of cannulated rod members 16, and a transverse connector 18 spanning between the pair of cannulated rod members 16. Each of the single axis pedicle screw assembly 12, poly-axial pedicle screw assembly 14, cannulated rod member 16, and transverse connector 18 form a unique and patentable aspect of the present invention.

The spinal fixation system 10 is shown and described herein as a "single level" fixation system, meaning the single axis pedicle screw assemblies 12 will be fixed to a first vertebral body, the poly-axial pedicle screw assemblies 14 will be fixed to a second vertebral body (adjacent to the first vertebral body), the rod members 16 will be disposed on either side of (and generally parallel to) the midline of the spine, and the transverse connector 18 will span between the rod members 16 generally perpendicularly to the mid-line of the spine. Although shown and described herein as a "single level" construct, it will be appreciated that the spinal fixation system 10 of the present invention may be used in multi-level procedures without departing from the scope of the present invention.

Moreover, before addressing the specifics of each the single axis pedicle screw assembly 12, poly-axial pedicle screw assembly 14, cannulated rod member 16, and transverse connector 18, it is to be appreciated that the combination shown in FIG. 1 is set forth by way of example only. That is, the spinal fixation system 10 of the present invention may comprise any number of variations of that shown without departing from the scope of the invention. For example, the spinal fixation system 10 may comprise four (4) of the single axis pedicle screw assemblies 12, four (4) of the poly-axial pedicle screw assemblies 14, and/or any combination of single and poly-axial pedicle screw assemblies 12, 14, in conjunction with the rod members 16 to effect spinal fixation.

Each single axis pedicle screw assembly 12 of the present invention includes a screw member 20 having a shaft 22 and a housing 24, as well as a locking screw 26. The shaft 22 and housing 24 are integrally formed as a unitary article such that the shaft 22 and housing 24 are in fixed relation, hence the term "single axis" to describe this type of pedicle screw assembly 12 according to the present invention. The shaft 22 includes a thread 28 suitable for introduction into and purchase within bone. Each housing 24 includes first and second branches 30, 32, which collectively form a generally "U" shaped area dimensioned to receive at least one of a ball portion 34 and/or a rod portion 36 (forming either end of the rod member 16 according to a further aspect of the present invention) and thereafter the locking screw 26. In a preferred aspect, each component of the fixed angle pedicle screw assembly 12 is cannulated (i.e. it is equipped with a longitudinal lumen extends through the locking screw 26 and screw member 20) such that a K-wire may be used to guide the fixed angle pedicle screw assembly 12 into the patient.

Each poly-axial pedicle screw assembly 14 of the present invention includes a screw member 40, a housing 44, and a locking screw 46. The screw member 40 includes a shaft 42. The screw member 40 and housing 44 are separate articles such that the angle of the housing 44 relative to the screw member 40 may be varied in any number of fashions prior to locking them together, hence the term "poly axial" to describe this type of pedicle screw assembly 14 according to the present invention. The shaft 42 includes a thread 48 suitable for introduction into and purchase within bone. Each housing 44 includes first and second branches 50, 52, which collectively form a generally "U" shaped area dimensioned to receive at least one of the ball portion 34 and/or rod portion 36 (forming either end of the rod member 16 according to a further aspect of the present invention) and thereafter the locking screw 46. In a preferred aspect, each component of the poly-axial pedicle screw assembly 14 is cannulated (i.e. it is equipped with a longitudinal lumen extends through the locking screw 46 and screw member 40) such that a K-wire may be used to guide the poly-axial pedicle screw assembly 14 into the patient.

The transverse connector 18 of the present invention includes a pair of rod clamping assemblies 60 capable of fixedly engaging regions on the respective rod members 16, as well as a linkage assembly 62 extending between the rod clamping assemblies 60. Each rod clamping assembly 60 includes a top clamp member 64, a bottom clamp member 66 (not shown), a clamp screw 68, and a poly-axial pivot ring 70 (not shown). The linkage assembly 62 includes a slotted link member 72, a grooved link member 74, and a link screw 76. The operation and details of the rod clamping and linkage assemblies 60, 62 will be described in greater detail below.

Figure 2:
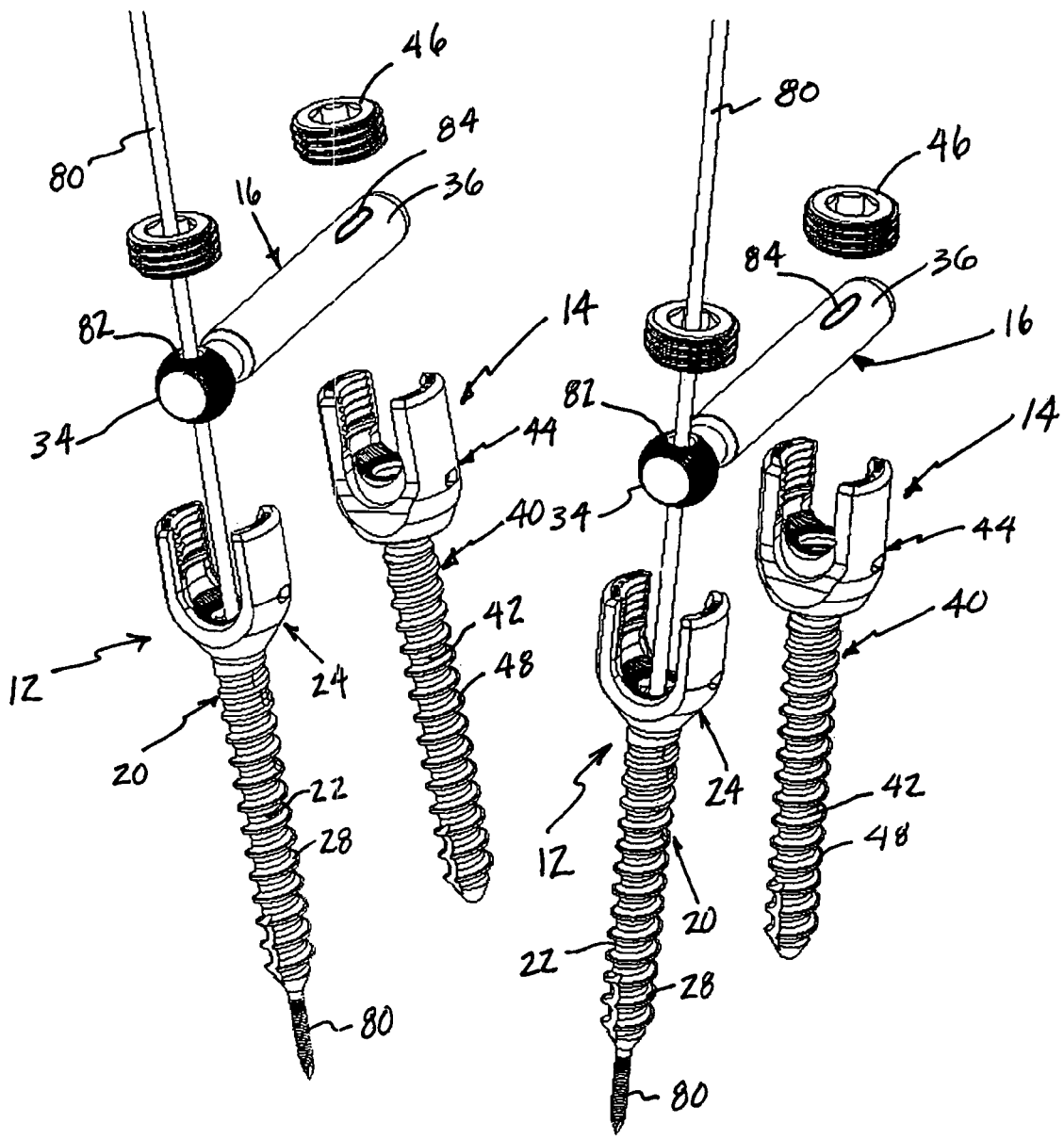
FIG. 2 is a perspective and exploded view of the spinal fixation system shown in FIG. 1 (sans transverse connector) illustrating the method of implanting the pedicle screws and rod member according to the present invention.

FIG. 2 illustrates a method of using the spinal fixation system 10 according to one embodiment of the present invention. As noted above, the fixed and poly-axial pedicle screw assemblies 12, 14 are preferably cannulated (i.e. a longitudinal lumen extends through the locking screws 26, 46 and screw members 20, 40, respectively). As such, each the pedicle screw assemblies 12, 14 of the present invention may be advanced over a K-wire 80 and thereby guided into the patient. More specifically, the K-wires 80 may be used (with or without image guidance, such as X-ray and/or fluoroscopy systems) to target the location and trajectory to introduce the shafts 22, 42 of the screw members 20, 40, respectively, into the pedicle of interest. Once the desired location and trajectory are identified, the screw members 20, 40 may be advanced over a respective K-wire 80 until the distal end of the shafts 22, 42 contact the pedicle, after which point the screw members 20, 40 may be rotated about the K-wire 80 (e.g., by rotating the housings 24, 44 via any suitable instrumentation) until the shafts 22, 42 are introduced a desired depth into the pedicle and/or vertebral body. This may be preceded by any number of suitable preparatory steps, such as drilling and/or tapping a pilot hole to better accommodate the shafts 22, 42 and/or threads 28, 48 prior to the introduction of screw members 20, 40.

Once the screw members 20, 40 have been introduced as described above, rod members 16 may thereafter be advanced into the patient for engagement with the pedicle screw assemblies 12, 14 of the present invention. To facilitate this, the rod member 16 may be provided with one or more cannulations (e.g. cannulation 82 in the ball portion 34 and/or cannulation 84 in the rod region 36) such that one or more ends of the rod member 16 may be guided over a K-wire 80 and into a respective housing 24, 44. Although described herein with the ball portion 34 engaging within the housing 24 of the fixed angle pedicle screw assemblies 12 and the rod portion 36 engaging within the housing 44 of the poly-axial pedicle screw assembly 14, it will be appreciated that this may be reversed in one or both sides without departing from the scope of the present invention. Any number of suitable instruments may be employed to facilitate the above-identified step, including but not limited to a pushing or holding device for guiding the rod member 16 into the patient.

After the rod member 16 is introduced as described above, the locking screws 26, 46 may thereafter be introduced and engaged with the housings 24, 44. It may be desirable to adjust the position of the rod member 16 relative to the pedicle screw assemblies 12, 14 according to a still further aspect of the present invention. More specifically, as will be discussed in greater detail below, the spherical nature of the ball region 34 of the rod member 16 will (prior to locking) allow it to rotate within the housing 24. As such, the ball region 34 will be loosely disposed within the housing 24 such that the remainder of the rod member 16 may be angled therefrom in any number of desired manners (e.g. up, down, side-to-side and/or any variation thereof) depending upon the situation and need. This may advantageously facilitate positioning the rod region 36 into the housing 44 after the ball region 34 has already been positioned within housing 24. Moreover, this may reduce if not eliminate the need to bend the rod member 16 as with traditional rod members of prior art pedicle screw systems.

It may be preferred to distract the screw members 20, 40 prior to fully locking the locking screws 26, 46 within the housings 24, 44. In this fashion, the surgeon can ensure that the proper disk height is attained prior to locking the rod members 16 to the pedicle screw assemblies 12, 14. This screw distraction may be accomplished using any number of suitable instruments. The locking screws 26, 46 may be secured or locked within the respective housing 24, 44 via any number of suitable mechanisms, including but not limited to the manner shown, namely threading the exterior of the locking screws 26, 46 and providing grooves along the interior of the housings 24, 44.

The spinal fixation system 10 of the present invention is suitable for both open and/or percutaneous procedures. In an open procedure, any or all of the components of the pedicle screw systems 12, 14 and rod member 16 may be introduced without the assistance of a K-wire (and, for that matter, such components may be non-cannulated). During a percutaneous procedure, however, both the pedicle screw assemblies 12, 14 and rod member 16 may be introduced percutaneously through the use of K-wire guidance. According to one embodiment, this may be accomplished by percutaneously (i.e. using a K-wire for guidance) introducing a first fixed pedicle screw assembly 12 into a first vertebral body, introducing a first poly-axial pedicle screw assembly 14 in an adjacent vertebral body, creating an incision extending between and down to the first fixed and poly-axial pedicle screw assemblies 12, 14, introducing the rod member 16 into the housings 24, 44, respectively, (optionally distracting), and introducing the locking screws 26, 46 to lock the rod member 16 relative to the pedicle screw assemblies 12, 14. In this fashion, the ball portion 34 of the rod member 16 will be locked in the housing 24 and the rod portion 36 will be locked in the housing 44. The K-wires 80 may then be withdrawn. Any number of suitable instruments may be employed to facilitate the above-identified steps, including but not limited to a screwdriver for screwing the locking screws 26, 46 into the housings 24, 44.

Figure 3:
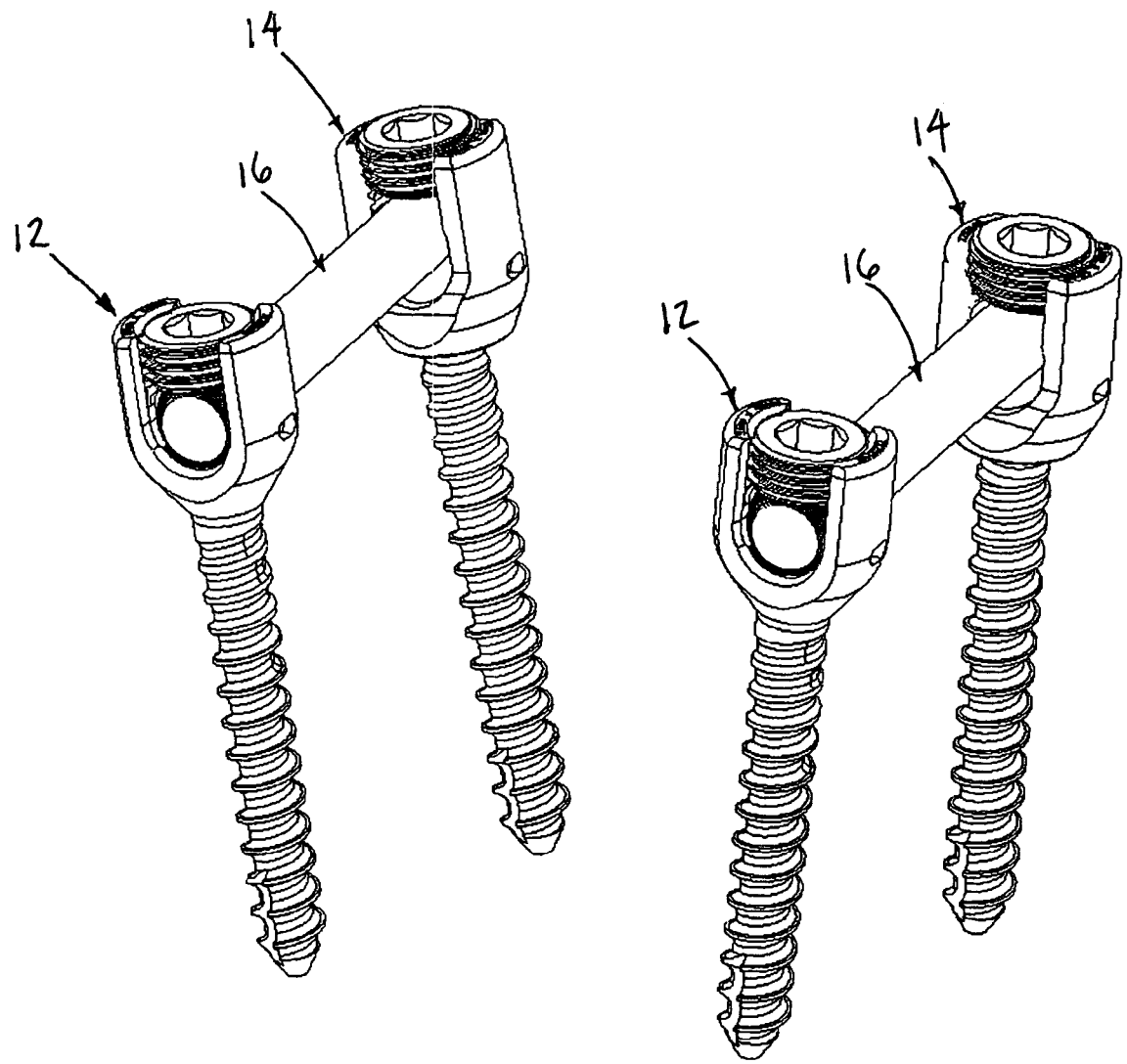
FIG. 3 is a perspective view of the spinal fixation system of the present (sans transverse connector) after implantation as shown in FIG. 2.
Figure 4:
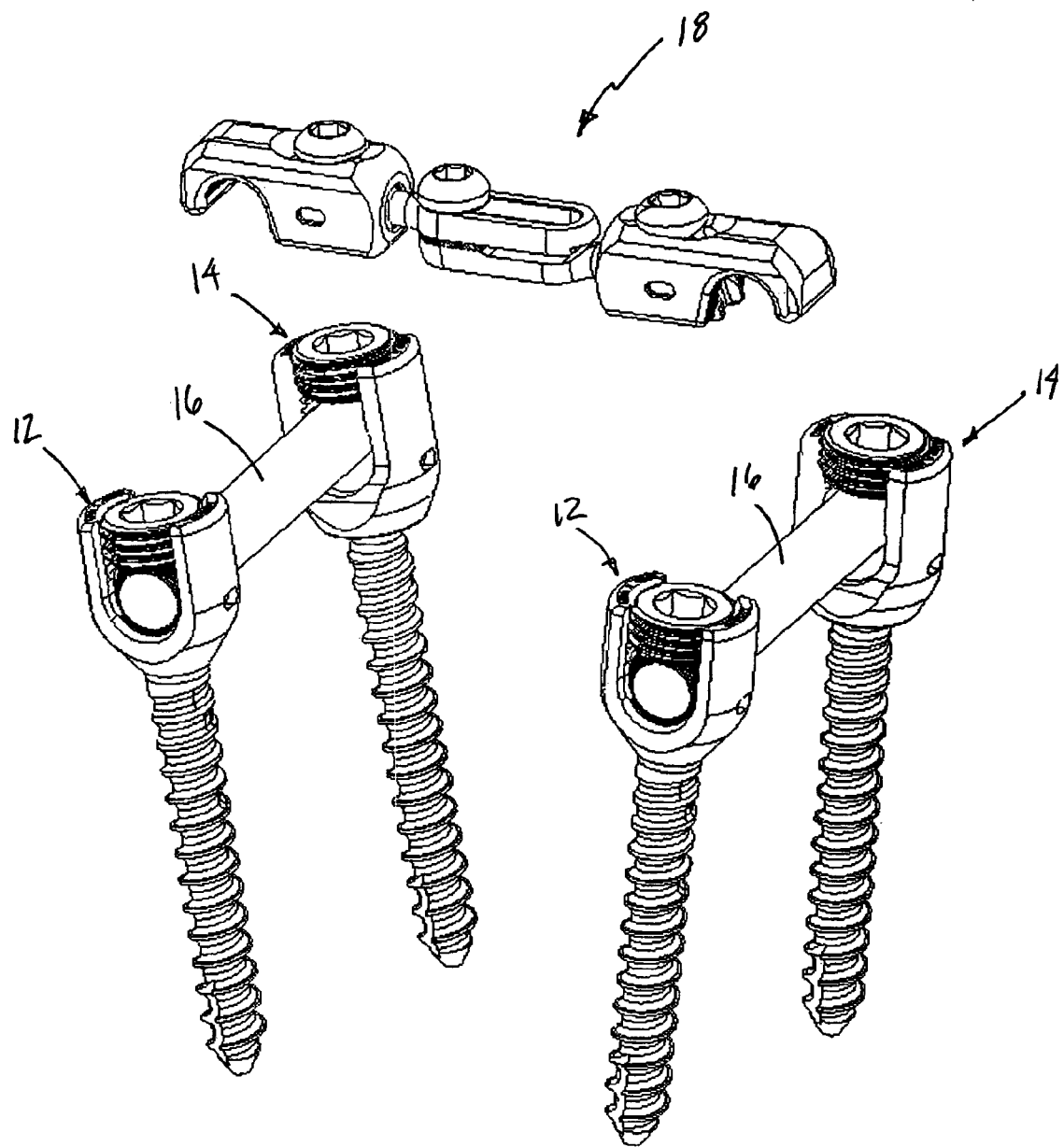
FIG. 4 is a perspective view of the transverse connector of the present invention being introduced onto the rod members of the spinal fixation system of the present invention.

In either event (open or percutaneous introduction), the spinal fixation system 10 of the present invention, once implanted, will appear as shown in FIG. 3. As shown in FIG. 4, the transverse connector 18 of the present invention may thereafter be employed to establish a rigid coupling between the adjacent rod members 16.

Figure 5:
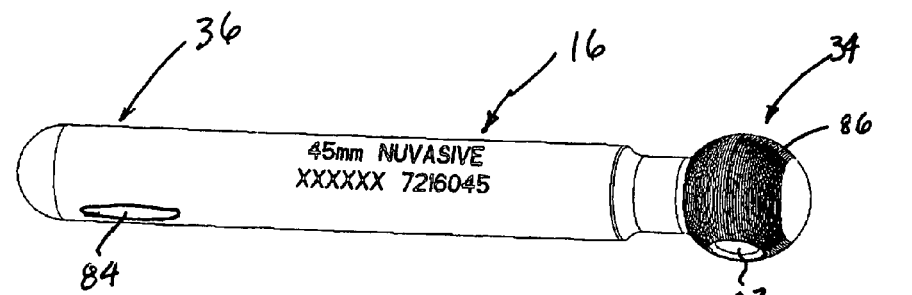
FIGS. 5-6 are side views of the rod member according to the present invention.
Figure 6:
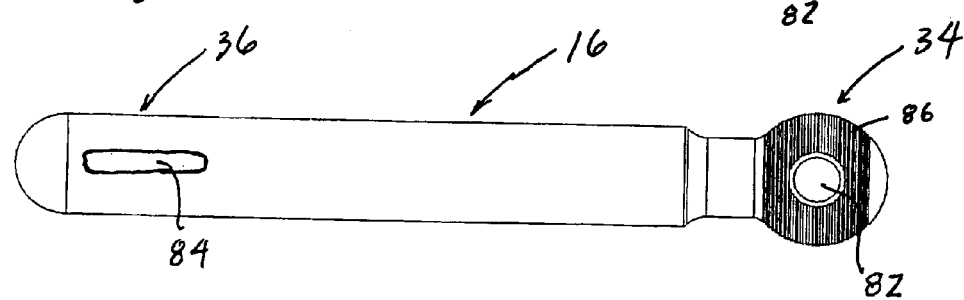

The rod member 16 will now be described in detail with reference to FIGS. 5-6. As set forth above, the rod member 16 of the present invention includes the ball portion 34 at one end and the rod portion 36 at the other end. According to the present invention, the ball portion 34 and/or the rod portion 36 may be cannulated for purposes of accommodating a K-wire for guiding the rod member 16 into the patient, such as represented by cannulations 82, 84. The cannulation 82 is preferably provided as a generally cylindrical lumen extending through the general center of the ball portion 34 such that it the center of the ball portion 34 may be guided directly into the spherical receiving area within the housing 24 (or housing 44 if the rod member 16 is reversed). The cannulation 84, on the other hand, has a generally elongated shape to accommodate variations in the distance between the housing 24 and housing 44, which may exist due to surgeon placement or other factors. According to the present invention, the ball portion 34 is equipped with a plurality of circumferential ridges 86 disposed generally perpendicularly to the longitudinal axis of the rod member 16. As will be described below, these circumferential ridges 86 cooperate with circumferential ridges provided within the housings 24, 44 such that, when the ball portion 34 is locked therein, the two areas of circumferential ridges engage and meld together to prevent any rotation or movement therebetween. The rod member 16 of the present invention may be of any length suitable or desirable to connect two or more vertebrae, and may be generally provided in a range of 25-300 mm.

Various aspects of the fixed angle pedicle screw assembly 12 of the present invention will now be described in detail with reference to FIGS. 7-9. According to one embodiment of the present invention, the interior of the first and second branches 30, 32 are provided with grooves 90 to threadedly engage with threads provided on the exterior of the locking screw 26. The grooves 90 and threads on the locking screw 26 may be configured such that the first and second branches 30, 32 are pulled together to prevent splaying during introduction of the locking screw 26 or due to use, such as by establishing a helical point-contact between the grooves 90 and threads on the locking screw 26. In a still further aspect of the present invention, the bottom of the housing 24 is provided with a plurality of circumferential grooves 92 and 94 dimensioned to engage with the circumferential grooves 86 on the ball portion 34 of the rod member 16. As mentioned above, this bolsters the purchase between the ball portion 34 and housing 26 such that the two are more effectively locked in position relative to one another after the locking screw 26 has been tightened. FIG. 8 best illustrates the "U" shaped opening in the housing 24, which may accommodate either the ball portion 34 and/or rod portion 36 of a rod member 16.

Figures 13, 14:
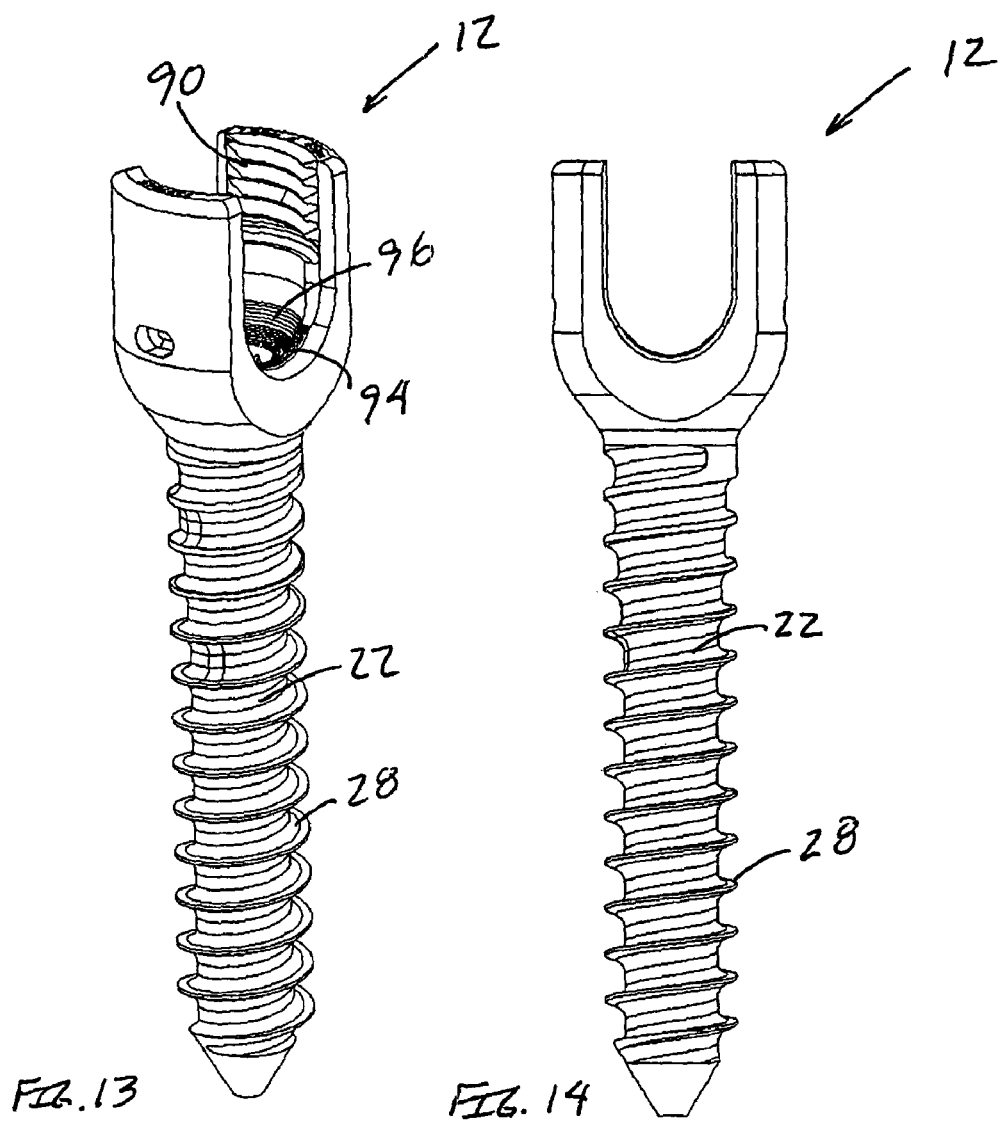
FIGS. 13-15 are perspective, side and top views, respectively, of a fixed angle pedicle screw assembly of the present invention, having a shaft diameter of 7.5 mm and a length of 45 mm.
Figure 15:
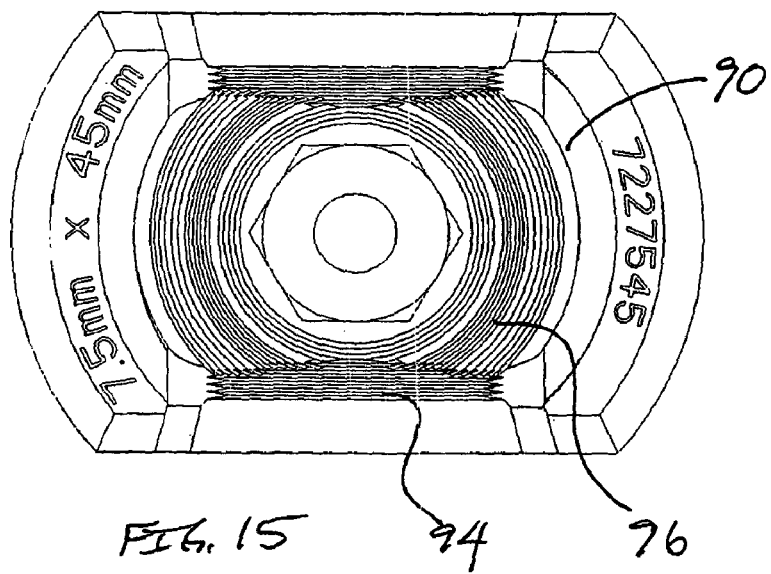

According to a still further aspect of the present invention, the thread 28 is designed to have a uniform pitch regardless of the diameter of the shaft 22. For example, as shown in FIGS. 10-12, the thread 28 has the same pitch for the 6.5 mm diameter shaft 22 as in the 5.5 mm diameter shaft 22 shown in FIGS. 7-9. In similar fashion, as shown in FIGS. 13-15, the thread 28 has the same pitch for the 7.5 mm diameter shaft 22 as in the 5.5 mm diameter shaft 22 shown in FIGS. 7-9 and the 6.5 mm diameter shaft 22 shown in FIGS. 10-12. This is advantageous, among other reasons, because it provides the ability to use the same cutting tools for all sizes of the thread form. The fixed angle pedicle screw assembly of the present invention may be of any length and width suitable or desirable to purchase the vertebrae, and may be generally provided with a width range of 5.5-7.5 mm and a length range of 30-50 mm.

Figure 16:
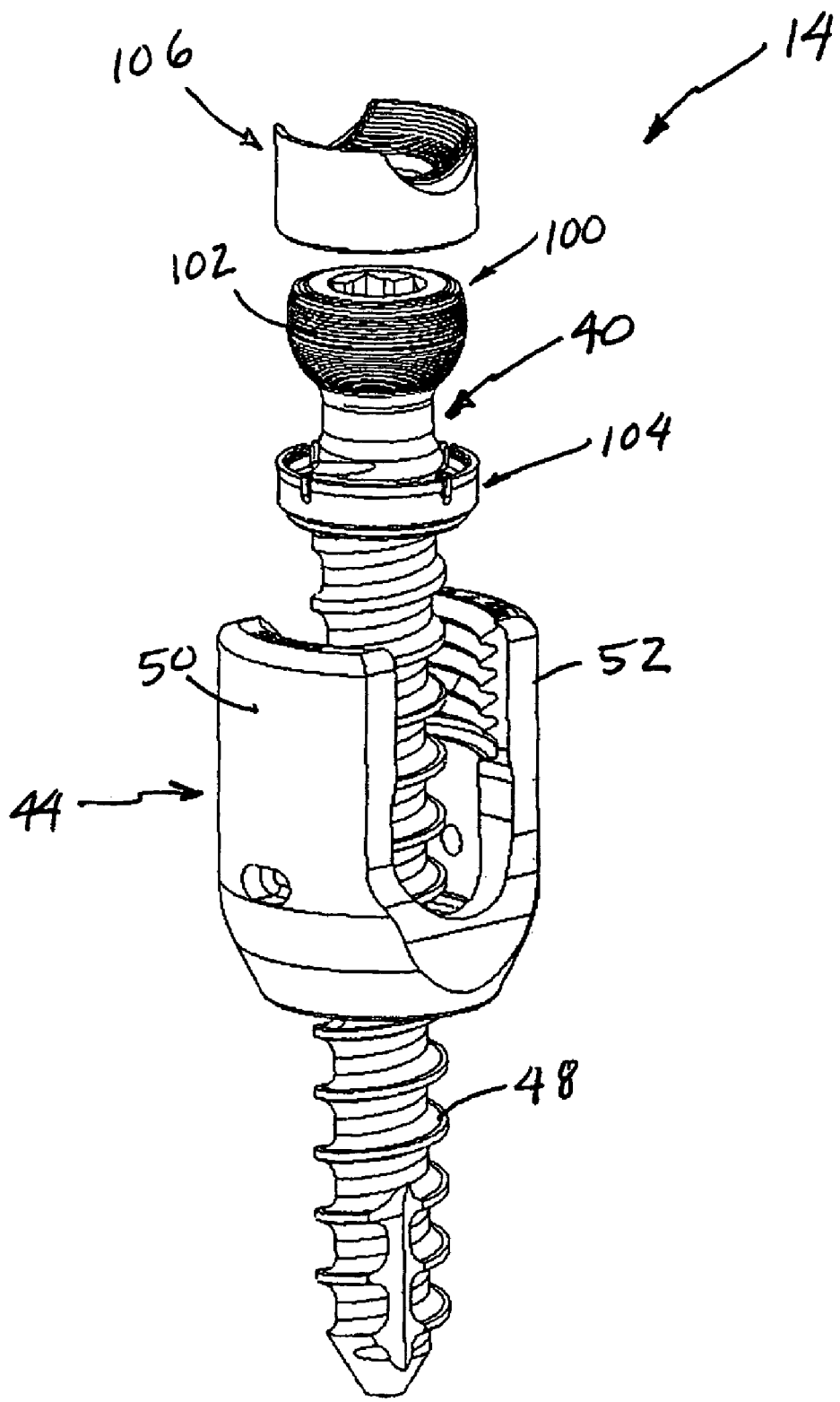
FIG. 16 is a perspective exploded view of a poly-axial pedicle screw assembly according to one embodiment of the present invention.
Figures 17, 18:
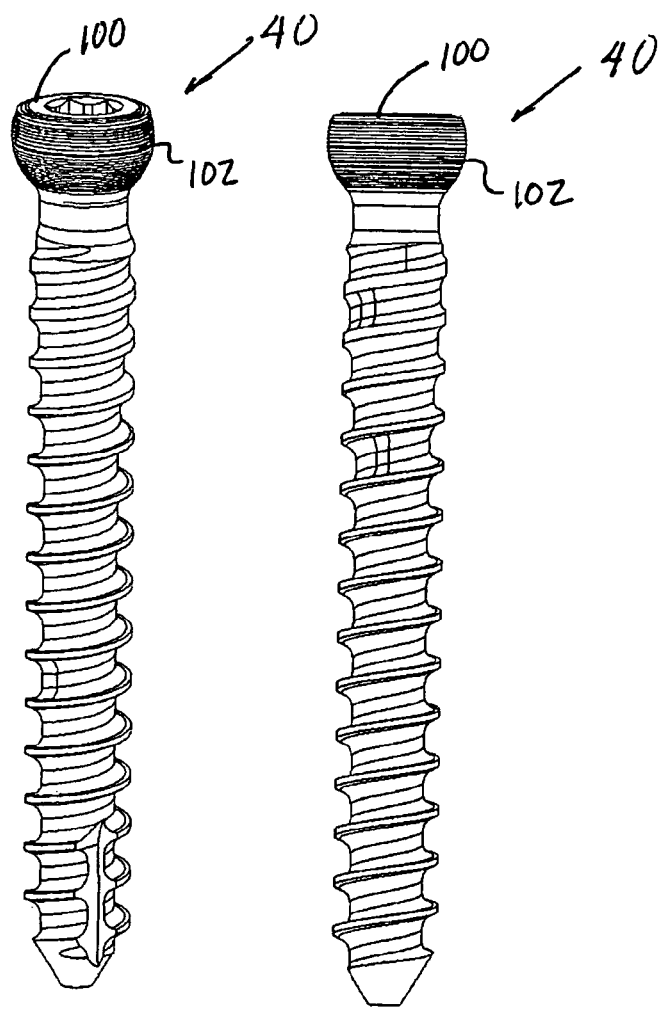
FIGS. 17-19 are perspective, side and top views, respectively, of a screw member forming part of the poly-axial pedicle screw system of the present invention.
Figure 19:
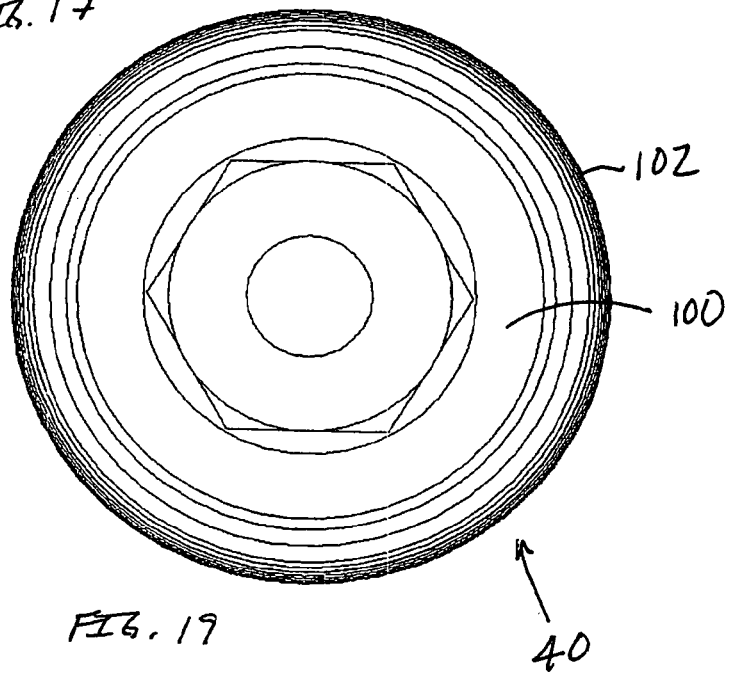
Figure 20:
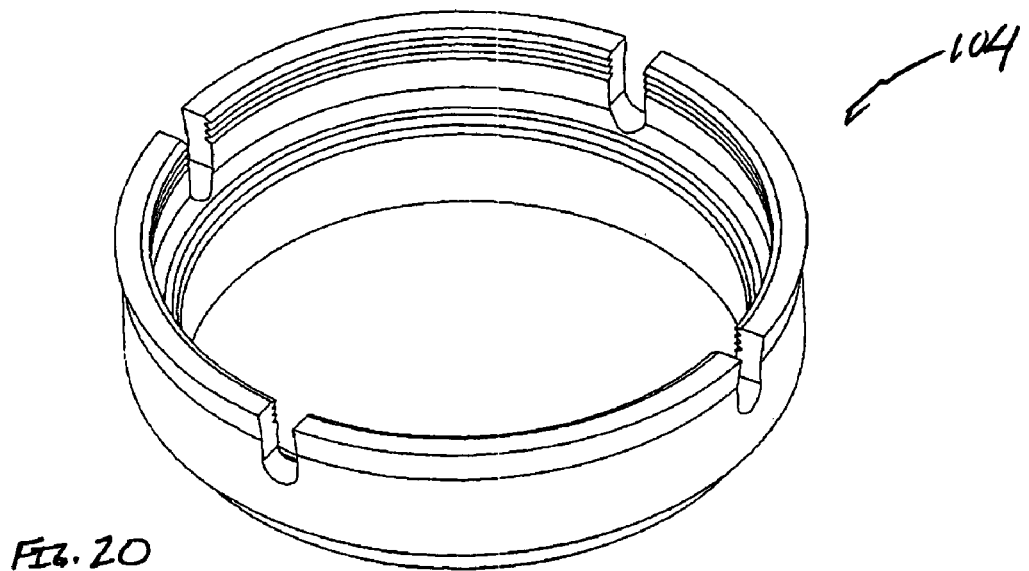
FIGS. 20-22 are perspective, side and top views, respectively, of a pivot ring forming part of the poly-axial pedicle screw system of the present invention.
Figure 21:
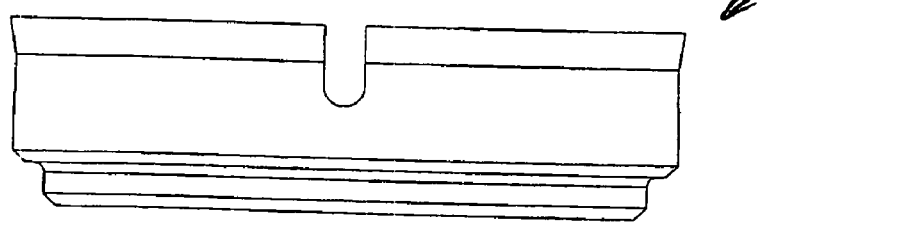
Figure 22:
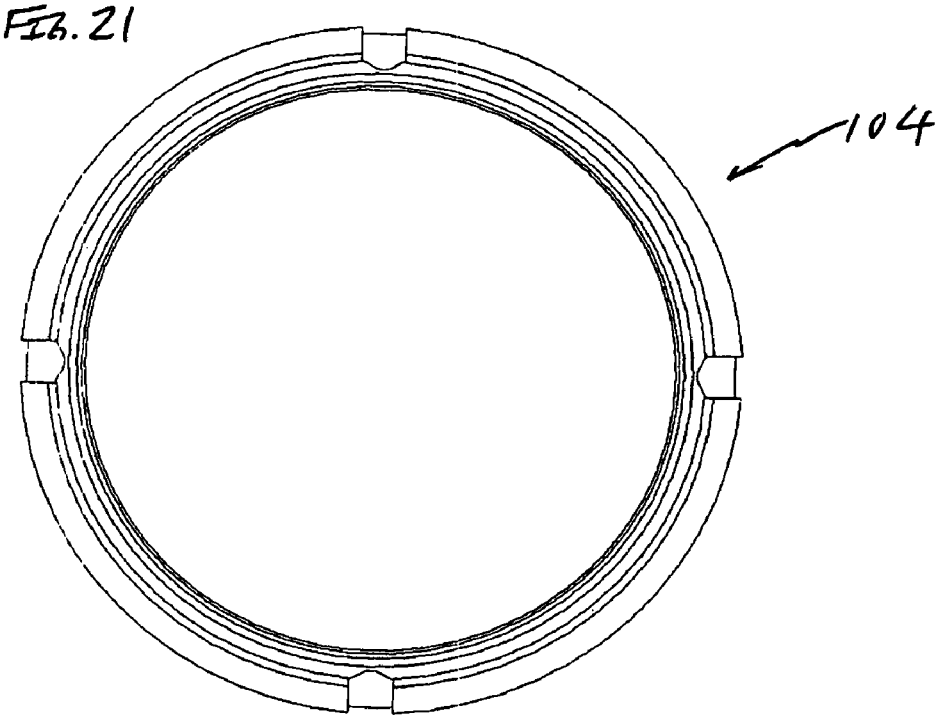

Various aspects of the poly-axial pedicle screw assembly 14 of the present invention will now be described in detail. As best shown in FIG. 16, the screw member 40 and a housing 44 are separate articles. With combined reference to FIGS. 16-19, the screw member 40 includes a hemi-spherical head region 100, which according to a preferred embodiment is equipped with a plurality of circumferential grooves 102. As best shown in FIG. 19, the screw member 40 is cannulated to receive a K-wire for guidance and includes a hex-type receiving area in the head region 100 to receive a screwdriver instrument. To facilitate the cooperation and engagement between the screw member 40 and the housing 44, the poly-axial pedicle screw assembly 14 is provided with a pivot ring 104 and a load ring 106. With combined reference to FIGS. 16 and 20-22, the pivot ring 104 is dimensioned to rest within a region within the bottom of the housing 44 and allow the head region 100 to pivot within the housing 44 prior to being locked in position. With combined reference to FIGS. 16 and 23-26, the load ring 106 will rest on top of the head portion 100 of the screw member 40 and forms the receiving area for the ball portion 34 and/or rod portion 36 of the rod member 16 of the present invention. To facilitate this, the load ring 106 is equipped with a plurality of circumferential grooves 108 and 110 to engage and lock with the circumferential grooves 86 provided on at least the ball portion 34. The poly-axial pedicle screw assembly of the present invention may be of any length and width suitable or desirable to purchase the vertebrae, and may be generally provided with a width range of 5.5-7.5 mm and a length range of 30-55 mm.

Figure 27:
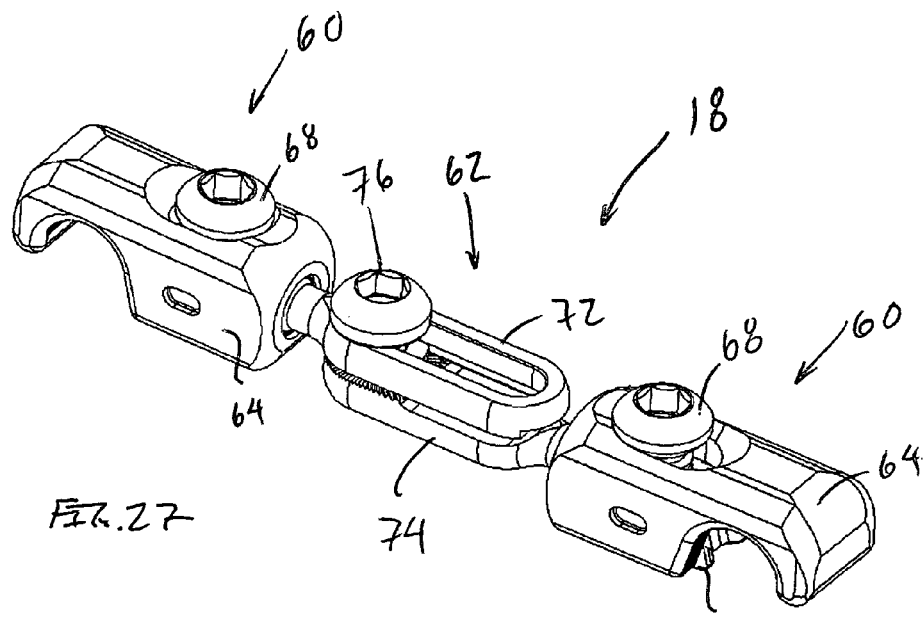
FIGS. 27-29 are perspective, side and top views, respectively, of a transverse connector according to the present invention.
Figure 28:
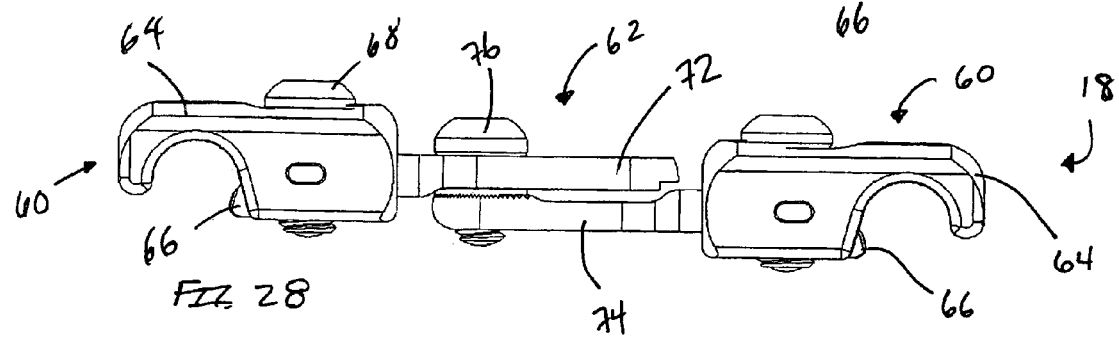
Figure 29:
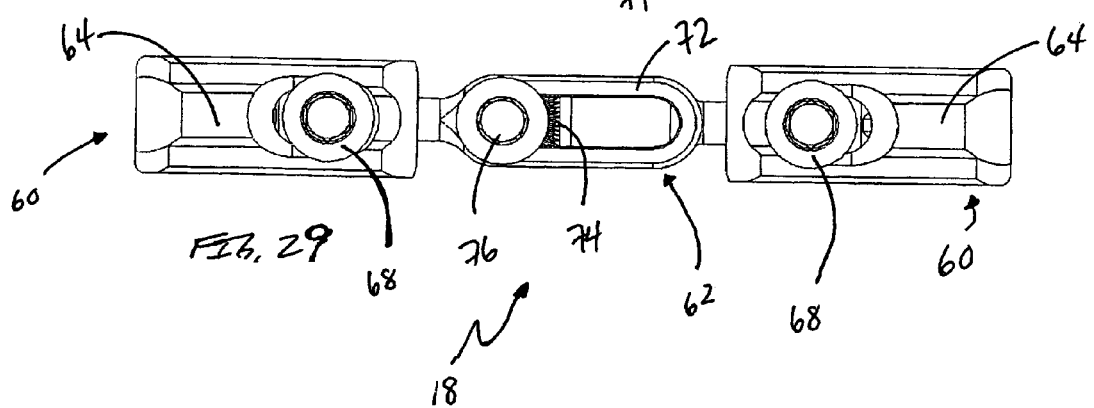

With reference to FIGS. 27-29, the transverse connector 18 of the present invention includes a pair of rod clamping assemblies 60 capable of fixedly engaging regions on the respective rod members 16, as well as a linkage assembly 62 extending between the rod clamping assemblies 60. Each rod clamping assembly 60 includes a top clamp member 64, a bottom clamp member 66 (not shown), a clamp screw 68, and a poly-axial pivot ring 70 (not shown). The linkage assembly 62 includes a slotted link member 72, a grooved link member 74, and a link screw 76. The transverse of the present invention may be of any length suitable or desirable to stabilize a pair of rods, and may be generally provided with a length range of 45-100 mm.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention.

What is claimed is:

1. A method for fixing at least two vertebrae in a spine, comprising the steps of:
   (a) advancing a K-wire to a first of said at least two vertebrae;
   (b) anchoring a first connector body in said first vertebra, said connector body having an anchor portion and a receiver portion, wherein said anchor portion is cannulated and is advanced to said first vertebra over said K-wire, said K-wire extending from said anchor portion and through an interior space of said receiver portion after said first connector body is anchored into said first vertebra;
   (c) anchoring a second connector body in a second of said at least two vertebrae, said second connector body having an anchor portion and a receiver portion;
   (d) connecting said first and second connector bodies with a rigid elongated element, said rigid elongated element having a cannulated first end that is advanced over said K-wire into said first receiver portion and a cannulated second ends that is advanced over said K-wire into said second receiver portion; and
   (e) fastening said rigid elongated element into said first and second connector bodies.

2. The method of claim 1, wherein said first end of said rigid elongate element comprises a shaped end.

3. The method of claim 2, wherein said shaped end is at least partially spherical.

4. The method of claim 3, wherein said first cannulation comprises a cylindrical opening that intersects a longitudinal axis of said rigid elongate element.

5. The method of claim 3, wherein said second end is cylindrical.

6. The method of claim 3, comprising the additional step of advancing a second K-wire to said second vertebra.

7. The method of claim 6, wherein said second lower portion of said second connector body is cannulated and is advanced to said second vertebra along said second K-wire.

8. The method of claim 7, wherein said second end of said rigid elongate element includes a second cannulation and wherein said second end is advanced to said second upper portion of said second connector body along said second K-wire.

9. The method of claim 8, wherein said step of fastening said rigid elongate element comprises advancing a first cannulated fastener along said K-wire to engage said first upper portion and advancing a second cannulated fastener along said second K-wire to engage said second upper portion.

10. The method of claim 9, wherein said at least partially spherical first end includes a plurality of circumferential ridges.

11. The method of claim 1, wherein said first end is cylindrical.

12. The method of claim 11, wherein said first cannulation comprises an elongate slot that intersects a longitudinal axis of said elongate element.

13. The method of claim 11, wherein said second end comprises a shaped end.

14. The method of claim 13, wherein said shaped end is at least partially spherical.

15. The method of claim 1, comprising the additional step of advancing a second K-wire to said second vertebra and wherein said second lower portion of said second connector body is cannulated and is advanced to said second vertebra along said second K-wire.

16. The method of claim 15, wherein said second end of said rigid elongate element includes a second cannulation and wherein said second end is advanced to said second upper portion of said second connector body along said second K-wire.

17. The method of claim 16, wherein at least one of said first end and said second end of said rigid elongate element is at least partially spherical.

18. The method of claim 1, wherein at least one of said first lower portion and said second lower portion comprises a pedicle screw.

19. The method of claim 18, wherein at least one of said first upper and lower portions and said second upper and lower portions are formed as a unitary article such that said at least one of said first upper and lower portions and said second upper and lower portions are fixed relative to one another.

20. The method of claim 19, wherein at least one of said first upper and lower portions and said second upper and lower portions are formed as separate articles coupled together such that said at least one of said first upper and lower portions and said second upper and lower portions are angularly moveable relative to one another prior to being locked in position.

* * * * *